United States Patent [19]

Rogers

[11] Patent Number: 5,360,742
[45] Date of Patent: Nov. 1, 1994

[54] EUKARYOTIC PLASMID VECTOR ENCODING ENZYMES FOR CYSTEINE PRODUCTION

[75] Inventor: George E. Rogers, Stonyfell, Australia

[73] Assignee: Luminis Pty. Ltd., Adelaide, Australia

[21] Appl. No.: 814,247

[22] Filed: Dec. 23, 1991

Related U.S. Application Data

[63] Continuation of Ser. No. 452,238, Dec. 18, 1989, abandoned.

[30] Foreign Application Priority Data

Dec. 19, 1988 [AU] Australia ............................... PJ2024

[51] Int. Cl.$^5$ .............................................. C12N 15/85
[52] U.S. Cl. .................... 435/320.1; 435/113; 435/172.3; 435/193; 435/195; 435/240.2; 435/252.3; 435/252.33; 536/23.2
[58] Field of Search ..................... 435/193, 195, 172.3, 435/113, 320.1, 240.2, 252.33, 252.3; 536/23.2

[56] References Cited

U.S. PATENT DOCUMENTS 4,870,013  9/1989  Gelfand et al. ..................... 435/69.1

OTHER PUBLICATIONS

Maniatis et al. Molecular Cloning: A Lab. Guide, CSH 1982 pp. 11–15.
Hulanicka et al *J. Bact.* vol. 168(1) pp. 322–327 Oct. 1986.
Sirko et al *J Gen Micro* 1987 vol. 133 pp. 2719–2725.
Denk et al. *J Gen Micro* 1987 vol. 133 pp. 515–525.
Monroe et al. *J. Bact.* vol. 170(1) pp. 42–47, Jan. 1988.
Robins et al. *Cell* vol. 29 pp. 623–631, Jun. 1982.
Gough et al., "Structure and Expression of the mRNA for Murine Granulocyte-Macrophage Colony Stimulating Factor", *The EMBO Journal*, 4:645–653 (1985).
Hulanicka et al., "The Structural Gene for O-Acetylserine Sulfhydrylase A in *Salmonella typhimurium*", *J. Biol. Chem.*, 249:867–872 (1974).
Hulanicka et al., "Regulation of O-Acetylserine Sulfhydrylase B by L-Cysteine in *Salmonella typhimurium*", *J. Bacteriol.*, 140:141–146 (1979).
Mauer et al., "Functional Interchangeability of DNA Replication Genes in *Salmonella typhimurium* and *Escherichia coli* Demonstrated by a General Complementation Procedure", *Genetics*, 108:1–23 (1984).
Nakamura et al., "Enzymatic Proof for the Identify of the S-Sulfocysteine Synthase and Cysteine Synthase B of *Salmonella typhimurium*", *J. Bacteriol.*, 158:1122–1127 (1984).
Ostrowski, "DNA Sequences of the cysB Regions of *Salmonella typhimurium* and *Escherichia coli*", *J. Biol. Chem*, 262:5999–6005 (1987).
Sanderson et al., "F+, Hfr, and F' Strains of *Salmonella typhimurium* and *Salmonella abony*", *Bacteriol. Rev.*, 36:608–637.
D'Andrea et al., "Isolation of Microbial Genes for Cysteine Synthesis and Prospects for Their Use in Increasing Wool Growth", *The Biology of Wool and Hair*, (Chapman & Hall Publishers, London), 447–463 (1989).
D'Andrea et al., "Increasing Wool Growth by Genetic Engineering Expression of Microbial Genes Encoding A Cysteine Pathway in Animal Cells", *Genome* (Suppl. 1), 30:444 (1988) (Abstract 35.21.8).
Rogers et al., "Towards a New Sheet Genotype with Increased Wool Growth by Transgenesis with Microbial Genes for Cysteine Synthesis", *J. Cell. Biochem.* (Suppl. 13B), 183 (1989) (Abstract F 222).

Primary Examiner—Richard A. Schwartz
Assistant Examiner—J. LeGuyader
Attorney, Agent, or Firm—Merchant, Gould, Smith, Edell, Welter & Schmidt

[57] ABSTRACT

The claimed invention provides a eukaryotic plasmid vector which upon expression provides the enzymes required for cysteine biosynthesis, the vector preferably allowing for expression of these enzymes and concomitant production of cysteine in ruminal mucosa cells. The vector of the instant invention is engineered using recombinant techniques to insert microbial genes encoding serine acetyltransferase (SAT) and O-acetylserine sulphydrolase (OASS), preferably the isolated *Salmonella typhimurium* genes cysE encoding for SAT and cysK or cysM encoding for OASS, driven by a promoter efficient in a eukaryotic host cell, such as the SV40 late promoter, into a eukaryotic cloning vector, such as Promega's pGEM-2. The construction of the instant vector also allows for an additional gene which upon expression produces human growth hormone.

7 Claims, 16 Drawing Sheets

FIG. 3 cysE gene from Salmonella Typhimurium

[Sequence figure showing the cysE gene from Salmonella Typhimurium with BamHI site at start, numbered nucleotide positions from 10 to 830, -35 and -10 promoter regions marked, a DdeI site boxed, a primer region underlined, and the translated amino acid sequence shown above the coding region.]

HeLa

CHO

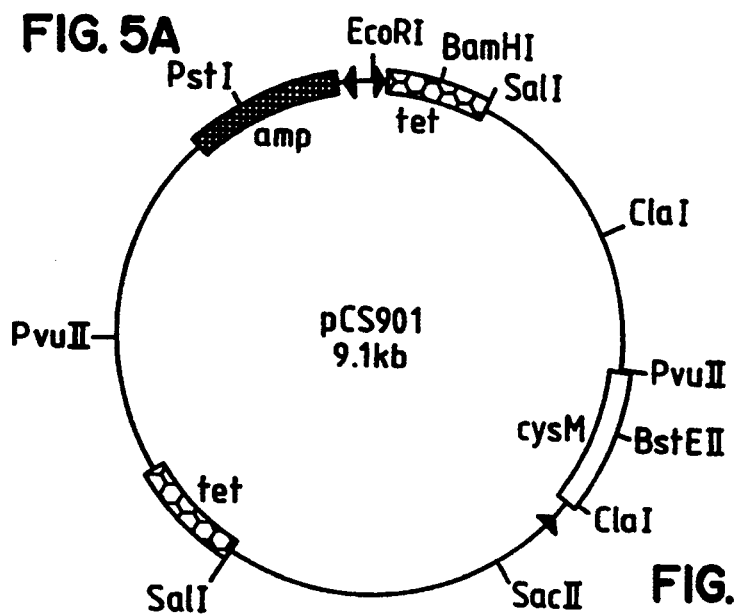
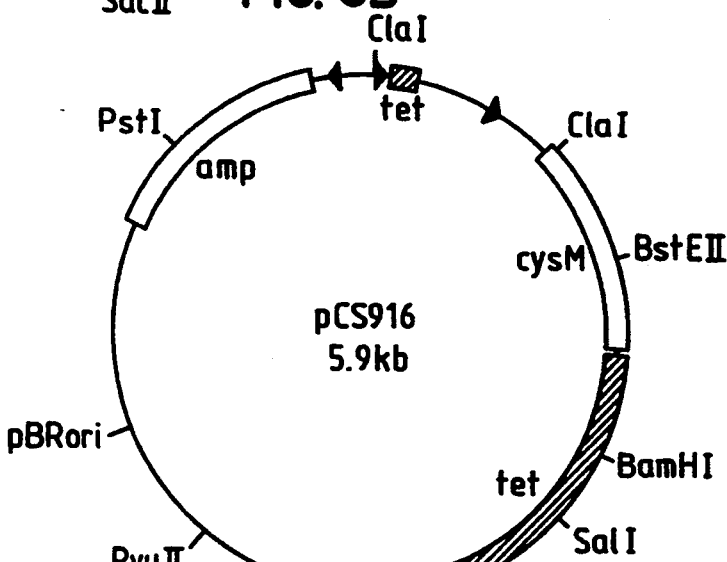
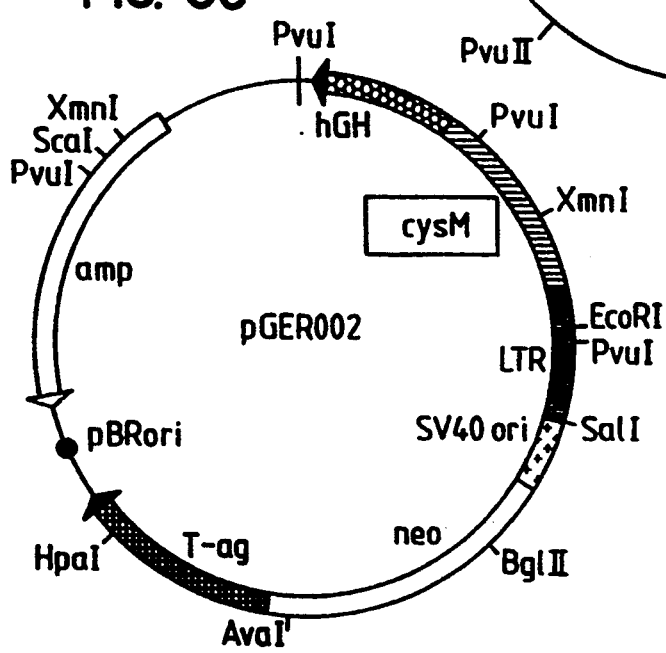

FIG. 6

```
CGGGGGGGGGGCAGTTTCACGTTCGGCCGGATCCGCTGGCCCTGGGCTATCCGCCCCGGGTACCAGGGGGCCGGTCGATCTGTTCCTGCGTCC       90
SacII          BssHII
GTGGGAGGTGGATATTAGCGCCCGGCACCAGCCTGGATTCGTCCTCTACCAGTCACAGTCTGCAGGTCACTATACAGT                      180
                                                CC
TAGTGGTACAGCCCTGGGTGGTGTATCACGATCCCCTGGTGGTGATGCCGGGCGGCGGTGTTCCGGTTCGGGCCGAGCGTTGTTTG              270
                                                     SmaI
TTGGACTGCGAAAAGCCGGGTCTGTATAACCCAGGTCGGTTATTGAAGCTGAAGAGGACTTGCTCTGGGCCATCGGGCCTGATAGG              360
                                           tR
TTAATTTGTATAGTTATCGGTCGGTGGGCTACGGCATACCGGGCTTTTTTACGAGCTGAAACGTGAATTACATTAGAACAACCATCGGC           450
                                                       -35     pgviM    -10
AATACGGCCGCTGGTCATTACAACGTCTGGGGCCGGATAACGGCAGTGAAATCTGGGTCAAGCTGGGAGGCATATATCCGGGCACGGATCG         540
                                                                                  RBS
                                                                  M K D R A L S M I V B A E K R G E I K P G D V L I E A T S
GTGAAAGATCGGGGCGGGCTATCGATGAATGTGTCGAGGGGGAAATTAACCGGGGGCGATGTCCTGATTGAAGGACCAGC                    630
                       HaeII,ClaI
```

FIG. 6 (cont.)

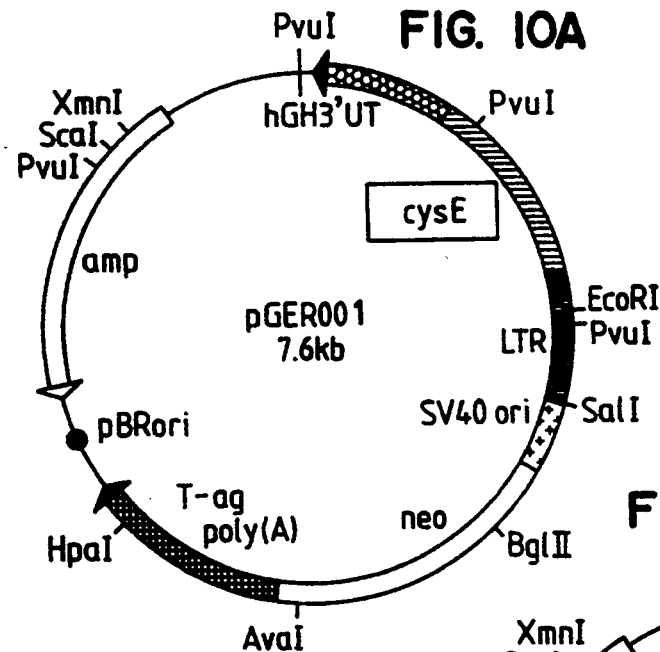
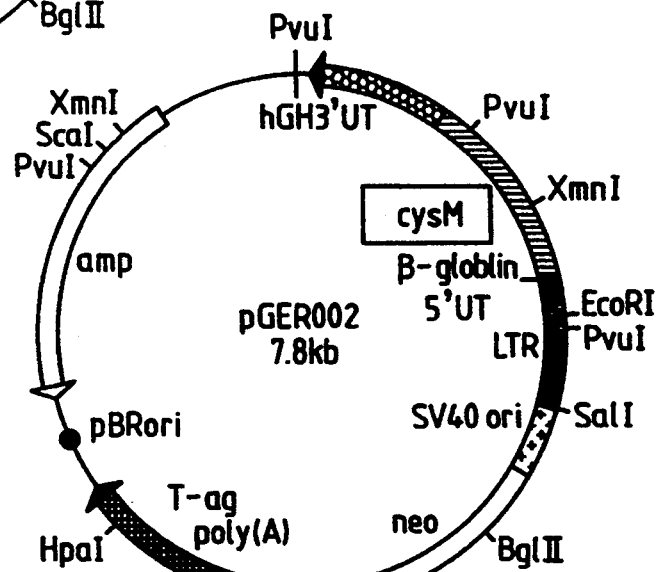
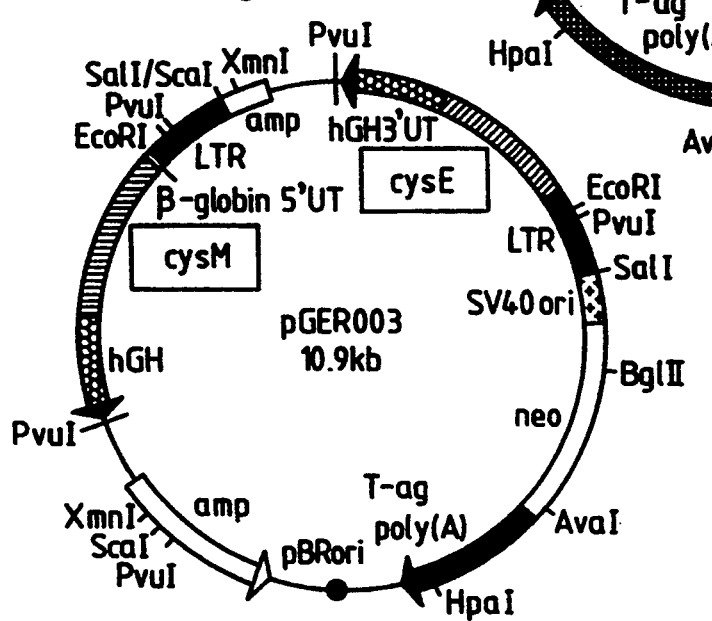

Identification of transgenic Sheep by PCR

Sulphydrylase Assay on Transgenic Sheep tissue

FIG. 14    Nucleotide sequence of the cysK gene of S. typhimurium

TATGGAAATAAGGTAAAATGTGTAAATAAGAGATGGCTTATGCTGTCTCTTATTCCATACTGATAACCATTATTTCCATCAGCATATA
                                                                                    1170

```
                                                                            M  S
GATATGCGAAATCCTTACTTCCCCATATCTGGCTGGAAGGTATGCTGGAAGGTATCCCAATTTCATACAGTTAAGGACAGGCCATGAGT
                                                                  BclII              1260
```

```
 K  I  Y  E  D  N  S  L  T  I  G  H  T  P  L  V  R  L  N  R  I  G  N  G  R  I  L  A  K  V
AAGATTTATGAAGATAACTCGCTGACTATCGGTCATACGCCGCTGGTTCGACTGAACCGTATCGGTAATGGACGCATTCTGGCAAAGGTG
                                                                                    1350
```

```
 E  S  R  N  P  S  F  S  V  K  C  R  I  G  A  N  N  I  V  D  A  E  K  R  G  V  L  K  P  G
GAGTCGCGCAACCCGAGCTTCAGCGTCAAGTGCCGTATCGGGGCCAACAACATGATTTGGGATGCCGAAAAGCGTGGCGTACTGAAACCTGGGC
                                                                                    1440
```

```
 V  E  L  V  E  P  T  N  G  N  T  G  I  A  L  A  Y  V  A  A  A  R  G  Y  K  L  T  L  T  M
GTGGAACTGGTGGAGCCGACCAACGGCAACACCGGTTATTGCGCTGGCGTATGTCGCCGCGGCGCGCGGTTACAAACTCACCCTGACCATG
                                                                                    1530
```

```
 P  E  T  M  S  I  E  R  R  K  L  L  K  A  L  G  A  N  L  V  L  T  E  G  A  K  G  M  K  G
CCGGAAACCATGAGCATTGAGCGTCGAAAGCTGCTGAAAGCGCTACTCAAGGCTACTCAAGGATTAGGCGCGAATCTGGTGCTGACCGAAGGCGAAGGGCGAAGGC
                                                                                    1620
```

```
A I Q K A E E I V A S D P Q K Y L L L Q Q F S I P A I P E I
GCTATTCAGAAAGCCGAAGAAATTGTCGCCAGCGATCCGCAAAAATATCTCCTGCTGCAGCAGTTCAGCATCCCTGCAATCCCCGGAAATC
                                                                                         1710

M E K T G P E I V E D T D G Q V D V F I S G V G T G G T L
CATGAAAAAACCGGGCCCCGAAATCTGGGAAGACACCGATGGTCAGGTCGATGTGTTTATCTCCGGCGTCGGCACTGGCGGTACGTTA
         HaeIII                                                                          1800

T G V T R Y I K G T K G K T D L I T V A V E P T D S P V I A
ACCGGGGTCACGCGTTATATCAAGGGAACGAAGGGTAAAACCGATCTTATCACCGTTGCGGTAGAACCCACTGACTCCCCGGTTATTGCC
                                                                                         1890

Q A L A G E E I K P G P H K I Q G I G A G F I P G N L D L K
CAGGCGCTGGCTGGTGAAGAGATCAAACCAGGCCCGCATAAAATTCAGGGTATCGGGGCAGGCTTCATCCCGGGCAACCTGGATCTGAAA
                   HaeIII                                                               1980

L I D K V V G I T N E E A I S T A R R L H E E E V F L A G I
CTGATTGATAAAGTGGTTGGCATCACCAATGAAGAAGCTATTTCTACCGCGCGCCGTCTGCATGAAGAGGAAGTATTCCTGGCAGGAATT
                                                                                         2070

S S G A A V A A A L K L Q E D E S F T K K I V V I L P S S
TCTTCCGGCGCCGCCGTTGCTGCCGCGCTTAAGCTGCAGGAAGATGAAAGCTTTACCAAGAAAATAGTTGTGATTCTCCTACCTTCATCA
                                                            HindIII                      2160

G E R Y L S T A L F A D L F T E K E L Q Q *
GGTGAGCGTTATCTGAGCACCGCCGTTGTTGCCGGATCTCTTTACTGGAGAAAGAGCTACAGTGATGCCAGCATGTTAAAACGCGTTAA
                                                                                         2250

AAAAGCACCTTTTTGGGTGCTTTTTGTGGCCTGCTGCTTCAACTTTCACCTCACCTGGCATTGAATTCACCCTGCCGGAACTGGTATTTAAC
                        HaeIII                                                          2340
```

FIG. 14 (cont.)

EUKARYOTIC PLASMID VECTOR ENCODING ENZYMES FOR CYSTEINE PRODUCTION

This is a continuation, of application Ser. No. 07/452,238, filed Dec. 18, 1989, now abandoned.

The present invention relates to a method of cysteine biosynthesis utilising transgenic techniques, to specific plasmid vectors for use therein, and to processes for preparation of such vectors.

It is known that normal pellage growth in a number of animals is sub-optimal. For example, normal wool growth in sheep, in particular fine wool sheep is suboptimal at least in part due to a net loss of essential amino acids. For example, there is abundant evidence in the prior art that normal wool growth is sub-optimal because of a net loss of cysteine-sulphur during the microbial protein metabolism in the rumen. This is illustrated in that if the diet of the sheep is supplemented with cysteine (or methionine) substantial increase in wool growth may be achieved.

However, the pathway for cysteine biosynthesis, e.g. in microorganisms, which utilises serine acetyltransferase (SAT) and O-acetylserine sulphydrylase (OASS) is absent in sheep.

The synthesis of cysteine has been extensively studied in microorganisms; the two key reactions being as follows:

(1) serine + acetyl CoA → O-acetylserine + CoA (catalysed by serine acetyltransferase (SAT)).

(2) O-acetylserine + $H_2S$ → cysteine + acetate (catalysed by O-acetylserine sulphydrylase).

Whilst orally administered cysteine and methionine are without effect on wool growth. These amino acids are degraded in the rumen and the derived sulphur is released as sulphide. Some of this sulphide is re-utilised by the microbiol flora of the rumen and incorporated into sulphur amino acids of microbial protein. It has been clearly demonstrated, however, that if cysteine (or methionine) is infused directly into the abomasum to avoid the destructive action of the ruminal flora then there is a pronounced increase in the rate of wool growth. The increase in wool growth is approximately 50-100% over control animals and is divided between increases in both length and diameter of the wool fibres. Cysteine supplementation has been observed to cause changes in the composition of wool, specifically increases in the levels of the ultra-high-sulphur group of keratin proteins. There have, however, been no reports of any adverse alterations to the properties of wool.

Accordingly, it is an object of the present invention to overcome, or at least alleviate, one or more of the difficulties related to the prior art.

Accordingly, in a first aspect of the present invention there is provided a plasmid including
a eukaryotic plasmid cloning vector;
a first sequence of DNA containing genes encoding the synthesis of the enzyme serine acetyltransferase (SAT) or part thereof;
a second sequence of DNA containing genes encoding the synthesis of the enzyme O-acetylserine sulphydrylase (OASS) or part thereof, and
a third sequence of DNA encoding a eukaryotic promoter region.

The plasmid according to this aspect of the present invention may be incorporated into an animal ovum and subsequently provide a transgenic animal with the endogenous capacity to produce cysteine, an essential amino acid for wool growth as discussed above. The economic benefits which may flow therefrom may be substantial and versatile in that the transgenic animals could be capable of producing significantly more (10 to 50%) pellage mass in a year. In addition, such transgenic animals may be more productive in marginal nutritional conditions. The nutritional status of animals with an endogenous supply of cysteine may also benefit young animals and increase their total rate of growth and produce more muscle protein.

In the plasmid according to the present invention any suitable plasmid cloning vector may be used. A plasmid pBR322-derived plasmid cloning vector may be used. The SP6/T7 promoter vector pGEM2 and available from Promega Corporation has been found to be suitable.

The first sequence of DNA containing genes encoding the synthesis of SAT may include the cysE genes, or a fragment thereof, isolated from Salmonella typhimurium.

The second sequence of DNA containing genes encoding OASS may include the cysM genes or cysK genes, or a fragment thereof isolated from Salmonella typhimurium. Alternatively, the second sequence of DNA may contain the MET25 gene or a fragment thereof isolated from Saccharomyces cerevisiae.

The third sequence of DNA encoding a eukaryotic promoter region may be such as to direct specifically gene expression in the ruminal mucosa of the animal to be treated.

Accordingly, in a preferred aspect of the present invention there is provided a plasmid pGER003, pGER004 or pGER005 as hereinafter described.

In a preferred form of this aspect of the present invention the plasmid may further include a fourth sequence of DNA derived from human growth hormone and encoding the transcription termination and polyadenylation signals thereof.

In a further aspect of the present invention there is provided a plasmid including
a eukaryotic plasmid cloning vector including a first sequence of DNA containing genes encoding the synthesis of the enzyme serine acetyltransferase (SAT).

In a preferred form, the third sequence of DNA encoding a eukaryotic promoter region which may direct gene expression in the ruminal mucosa or part thereof.

In a further preferred form the plasmid may further include a fourth sequence of DNA derived from human growth hormone (hGH) encoding for transcription, termination and polyadenylation.

The plasmid cloning vector used may be a eukaryotic plasmid cloning vector pGEM-2 and available from Promega.

A plasmid bearing a first sequence of DNA containing genes encoding the synthesis of serine acetyltransferase (SAT) is known. The plasmid pRSM8 (Monroe and Kredich, 1988) contains a 2.3 kb BamHI/HindIII insert which includes the complete nucleotide sequence. A 1.5 kb BamHl/EcoRl fragment may be formed by digestion of the plasmid pRSM8. A further fragment 0.98 kb DdeI/EcoRl fragment may be formed therefrom. These may form the first sequence of DNA.

The eukaryotic promoter region may be derived from the long terminal repeat (LTR) promoter of Rous sarcoma virus (RSV) or from the SV40 late promoter. The LTR promoter of Rous sarcoma virus may be provided in the plasmid pRSVN.03. The SV40 promoter may be provided on the plasmid pJL-E.

Samples of bacterial strains bearing the plasmids pJL-E and pGER001 are maintained in the culture collections of the University of Adelaide, Adelaide, South Australia. The plasmid pJL-E is an SV40-based vector derived from pJL4 (Gough, et al. "Structure and expression of the mRNA for murine granulocyte-macrophage colony stimulating factor", The EMBO Journal Vol. 4, No. 3 pp 645-653, 1985) and contain the cysE gene sequence inserted at the SalI site of the polylinker downstream to the SV40 late promoter. A133 bp HpaI/BamIII isolated from pSV2CAT encompassing the polyadenylation signal sequences for SV40 early transcripts may be inserted into the SmaI site of the polylinker in pJL4 to provide necessary 3' end processing. pGER001 contained the cysE gene flanked upstream by the 0.85 kb RSVLTR promoter sequence and downstream by a 0.6 kb sequence from the 3' flanking region of the human growth hormone gene. This construct was derived from pRSVN.03 (a gift of A. Robins) by blunt-end cloning into the BamHI site and it also contained the neomycin-resistance gene enabling selection of stably-transfected cell lines with G418.

The plasmid cloning vector may be a eukaryotic cloning vector. The eukaryotic cloning vector pGEM2 and available from Promega Corporation may be used. The plasmid pGEM2 is an SP6/T7 promoter vector.

The second sequence of DNA containing genes encoding O-acetylserine sulphydrylase (OASS) may be defined as described below. A SacII-PvUII DNA sequence described in FIG. 6, or part thereof may define the second sequence of DNA. The SacII-PvUII DNA sequence encodes the cysM gene. In a preferred form, the DNA sequence may be modified such that the cysM gene indicates translation of a correct AUG site to produce active enzyme.

The plasmid pGER004 carries the modified cysM gene, so is the preferred plasmid for use in trangenesis. Further more it carries both genes required in a single plasmid. Thus both genes may integrate together in the same site of an animal genome.

The plasmid pGER004 carries two cysterine biosynthesis genes, cysE and cysM, under the transcriptional control of the RSVLTR promoter.

In an alternative aspect of the present invention, a HaeIII/HaeIII sequence described in FIG. 14, or part thereof, may define the second sequence of DNA. The HaeIII/HaeIII DNA sequence encodes the cysK gene.

The bacterial gene, cysK may be substituted for cysM, since its protein product (O-acetylserine sulphydrylase) has a higher affinity for the substrate, O-acetylserine, as compared to the cysM gene product. In the tissues of the transgenic animals this higher affinity may be an advantage if the substrate concentration is low. The plasmid pGER005 carries two cysterine biosynthesis genes, cysE and cysK, under the transcriptional control of the RSVLTR promoter.

The third sequence of DNA encoding a eukaryotic promoter region may be derived from Rous Sarcoma Virus LTR (RSVLTR). A plasmid pGER001, incorporating the cysM gene and a plasmid pGER002, incorporating the cysE gene are illustrated in FIG. 11. A sample of strains bearing the plasmids pGER001 and pGER002 are maintained in the culture collection of the University of Adelaide, Adelaide, South Australia.

In a still further aspect of the present invention there is provided a method of preparing a plasmid including
   a eukaryotic plasmid cloning vector;
   a first sequence of DNA containing genes encoding the synthesis of the enzyme serine acetyltransferase (SAT);
   a second sequence of DNA containing genes encoding O-acetylserine sulphydrylase (OASS): and
   a third sequence of DNA encoding a eukaryotic promoter region; and
   a fourth sequence of DNA encoding the transcription, termination and polyedeylation signals from human growth hormone (hGH) which method includes
   ligating the first sequence of DNA into a suitable restriction site on the plasmid cloning vector;
   ligating the second sequence of DNA into a suitable site on the plasmid cloning vector;
   ligating the third sequence of DNA to the 5' end of the second sequence of DNA; and
   ligating the fourth sequence of DNA to the 3' end of the second sequence of DNA.

In a preferred aspect, the method of preparing the plasmid may include
   providing
      a first plasmid pGER001 as hereinafter described; and
      a second plasmid pGER002 as hereinafter described;
   subjecting the second plasmid to a digestion to form a restriction fragment including the sequence of DNA encoding for the cysE gene; and
   ligating the fragment of DNA so formed into a suitable site in the first plasmid.

A 3.3 kb SalI/ScaI fragment may be excised from pGER002 and inserted into the ScaI site of pGER001 by blunt-end ligation. Recombinants may be selected on media containing ampicillin such that only those clones containing a tandem arrangement of the cysE and cysM genes (i.e. recombinants in which the B-lactamase or amp$^r$ gene was restored) were viable.

The plasmid so formed may be utilised in the treatment of the ovum of animals to provide for endogeneous synthesis of cysteine.

Accordingly, in a further aspect of the present invention there is provided a method of preparing a transgenic animal, which method includes
   providing
      a recently fertilised ovum from a female of the animal; and
      a plasmid as described above;
   injecting the plasmid into the male pronucleus prior to fusion with the female nucleus to form a single cell embryo; and
   subsequently implanting the ovum into a suitably prepared female animal.

Preferably the animal is a sheep.

The injection of the pronucleus may be carried out under magnification and use of standard microinjection apparatus. The ova may be held by a blunt holding pipette and the zona pellucida, plasma membrane and pronuclear envelope may be penetrated by an injection pipette. The blunt holding pipette may have a diameter of approximately 50 um. The injection pipette may have a diameter of approximately 1.5 um.

The amount of gene construct injected will necessarily be dependent upon the size of the pronucleus and the size of the injection pipette.

The egg may be subsequently implanted by any suitable method into any suitably prepared surrogate mother. This may be achieved by any known method.

The present invention will now be more fully described with reference to the accompanying Examples. It should be understood however that the following description is illustrative only and should not be taken in any way as a restriction on the generality of the invention described above.

IN THE FIGURES

FIG. 3 illustrates the complete nucleotide sequence of the cysE gene from *Salmonella Typhimurium*.

Figure 4A:
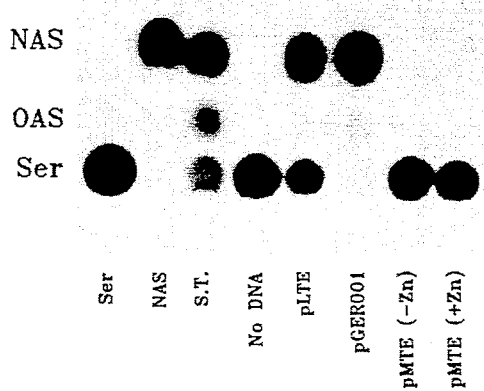
Figure 4B:
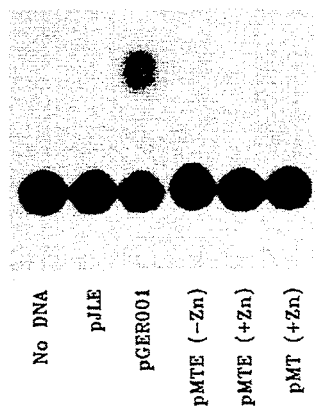
Figure 4C:
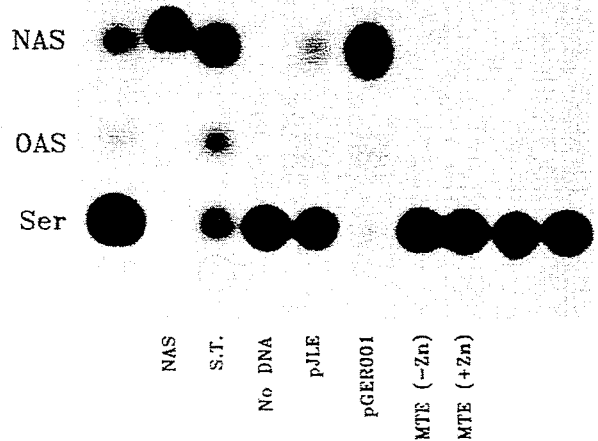

FIGS. 4A, 4B, and 4C illustrates transient expression of SAT from the CysE gene in plasmids pJLE and pGER001 on nitrocellulose.

FIGS. 5A, 5B, and 5C illustrates the restriction maps for plasmids pCS901, pCS916 and pGER002.

Figure 6:
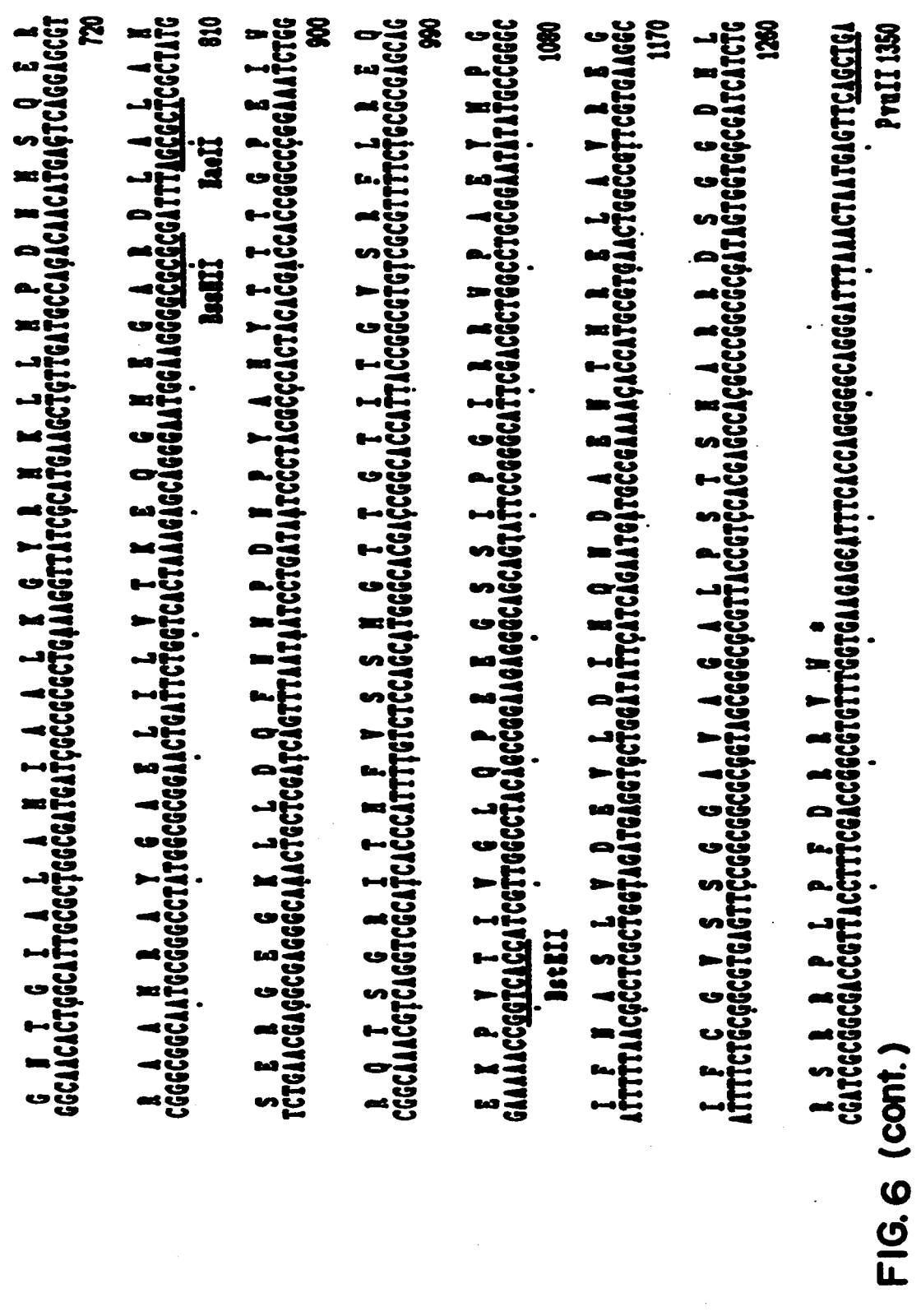

FIG. 6 illustrates the complete nucleotide sequence of the SacII-PvuII DNA fragment encoding the cysM gene. The sense strand is shown in the 5' to 3' direction. Potential terminator for the upstream transcript(s) and the promoter for cysM are marked as tM and p$^{cysM}$ respectively. When GUG is used as initiation codon the amino acid which starts the translation is methionine and to reflect this fact the GUG codon at 541 is marked with a Met instead of Val. The restriction sites referred to in the text are shown as also the most probable ribosome binding site (RBS) for cysM. The SmaI site at sequence position 231 was created during the oligonucleotide directed mutagenesis aimed at changing the ATG at 228 to ATC.

Figure 7:
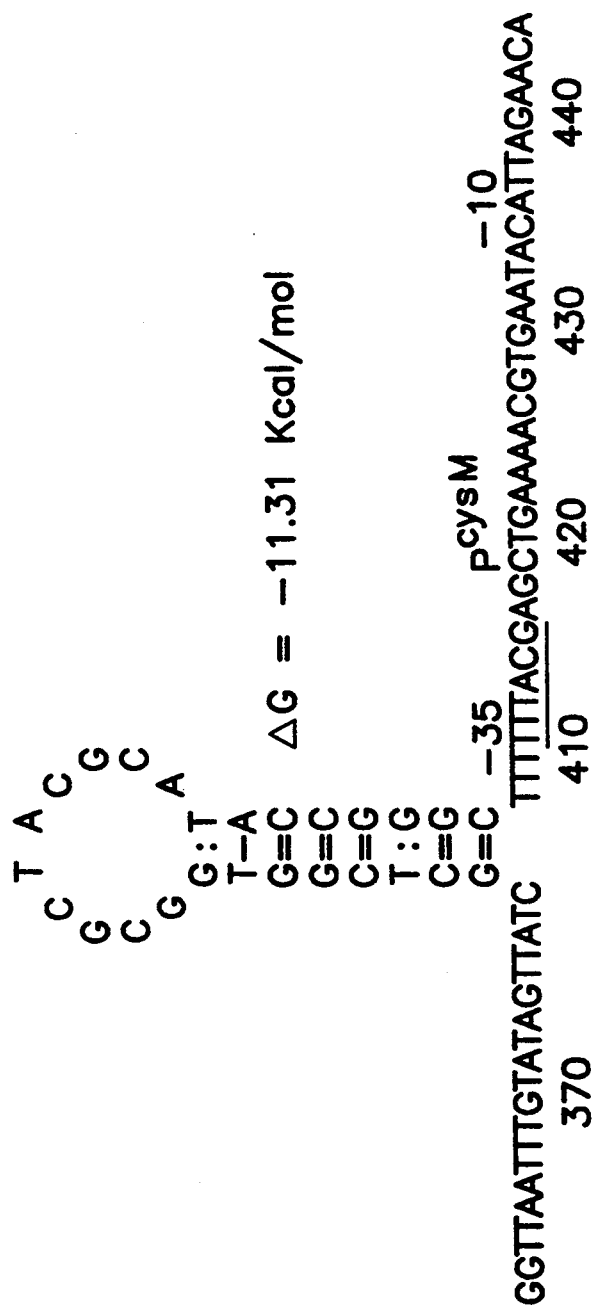

FIG. 7 illustrates the terminator and promoter sequences found before the cysM coding region.

Figure 8A:
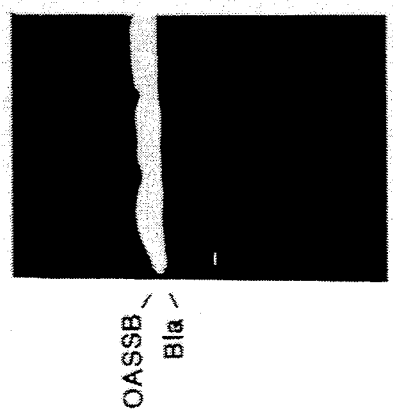

FIG. 8 illustrates:

FIG. 8(A)—Prokaryotic transcription/translation of plasmid DNA's carrying the cysM gene. (a)—pAT153, vector alone without any gene insert as control. (b)—pCS918, carries a frameshift mutation in the coding region of cysM. (c) pCS916, carries the wild type gene. The size of the shortened polypeptide, shown by arrow, has been estimated to be 21kDal.

Figure 8B:
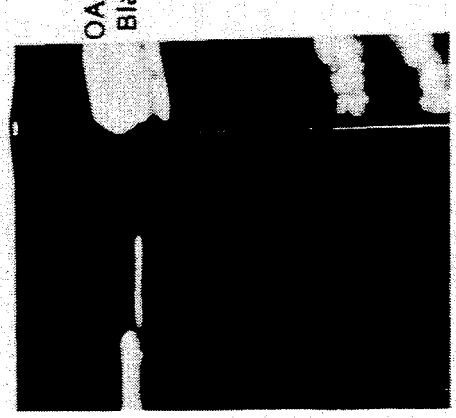

FIG. 8(B)—Translation of cysM in prokaryotic and eukaryotic systems. (a) and (b)—Rabbit reticulocyte lysate translation of pCS920 and pCS921, respectively. (c)—Control translation without any added mRNA, and (d) in vitro prokaryotic transcription/translation of pCS920.

Figure 8C:
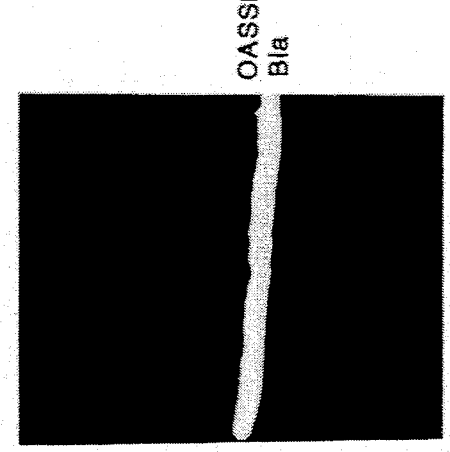

FIG. 8(C)—Prokaryotic transcription/translation of plasmids containing oligonucleotide directed changes to the GUG initiation codon. (a)—Wild type gene in pCS920, (b) Frameshift mutation in pCS921, (c) GUG to AUG change in pCS930 and (d) GUG to CGA change in pCS931.

Figure 9A:
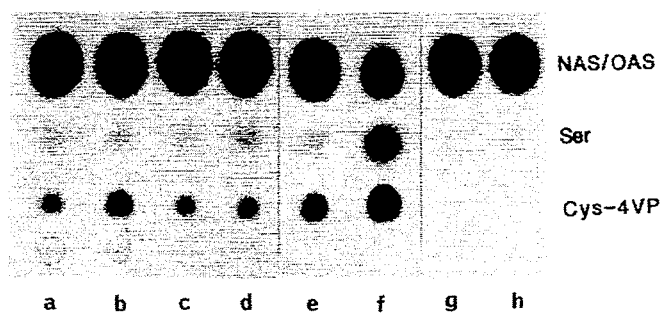

FIGS. 9A & B illustrates:

OASSB activity in extracts of stable transfected CHO cells. The 2-step assay was done as described in materials and methods and the products separated on thin layer chromatograph. (a) to (e)—Extracts from cells transfected with the cysM. (f)—Bacterial cell extract as positive control. (g) and (h) cells transfected with cysE and the vector DNA, respectively, as negative controls.

OASS-B activity in transgenic mice tissue. Sections of tails from 2-3 week old mice were homogenized in 10 mM Tris pH 7.5, 0.1 mM pyridoxal phosphate and freeze thawed several times to release the intracellular proteins. These cells extracts were assayed for OASS-B. (a)—(c) Tissue from mice transgenized with cysM. (d)—tissue from mouse transgenized with cysE and, (e)—Bacterial cell extract.

FIGS. 10A, 10B, and 10C illustrate the restriction maps for plasmids pGER001, pGER002 and pGER003. In the figure:

| | |
|---|---|
| LTR = | long terminal repeat from *Rous sarcoma* virus |
| SV40 ori = | origin of replication of SV40 virus |
| neo = | gene for resistance to the antibiotic, neomycin |
| T-ag = | part of the gene for T-antigen of SV40 virus |
| pBR ori = | origin of replication for the plasmid pBR322 |
| amp = | gene for resistance to the antibiotic, ampicillin |
| h GH 3'UT = | 3' end of the gene of human growth hormone |
| Cys M = | Cys M gene from *Salmonella typhirmurium* |
| Cys E = | Cys E gene from *Salmonella typhimurium* |
| B-globin 5'UT = | 5' untranslated region of the B-globin gene from the frog *Xenopus laevis* |

Figure 11:
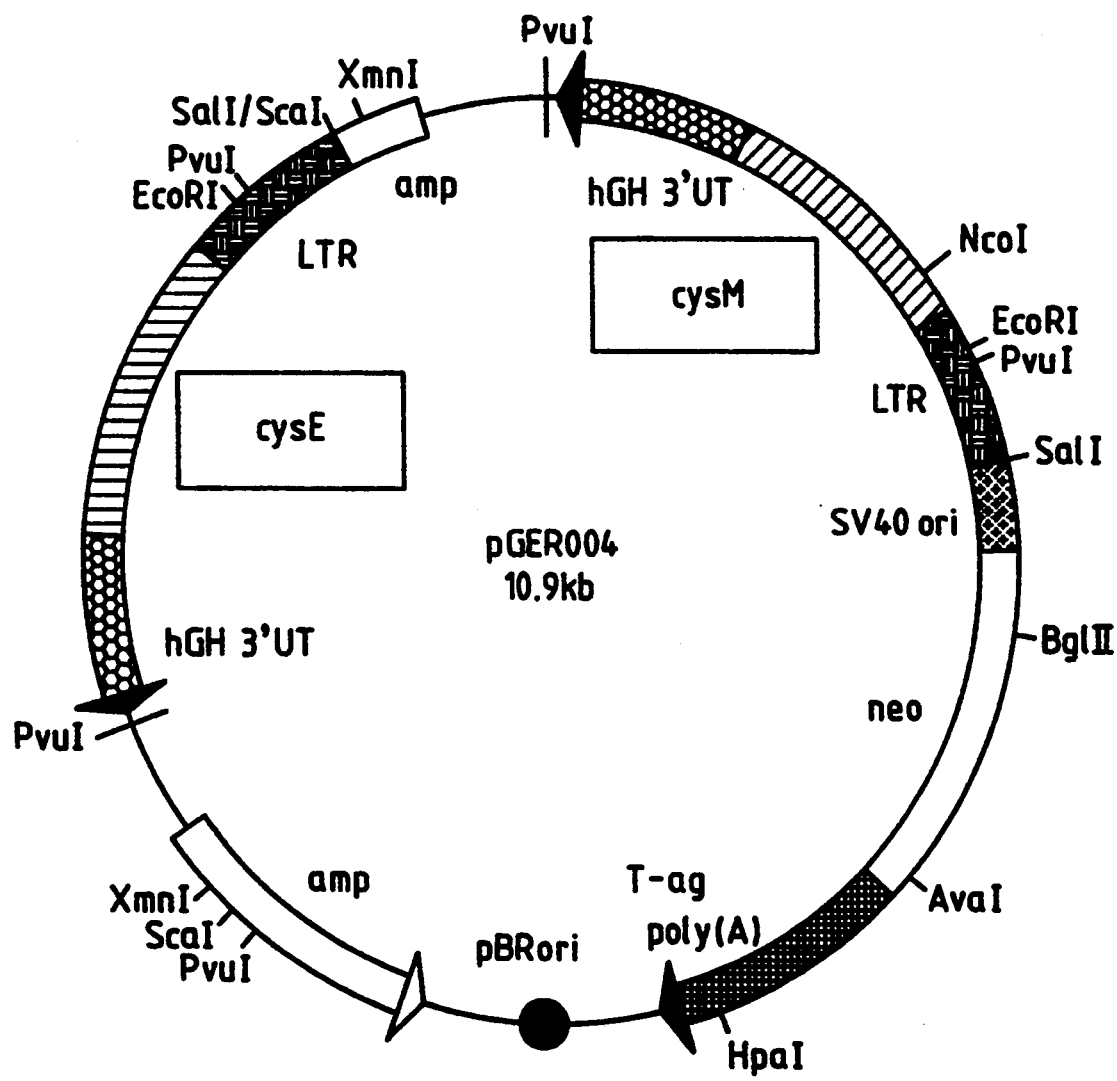

FIG. 11 illustrates the restriction map for plasmid pGER004.

Figure 12:
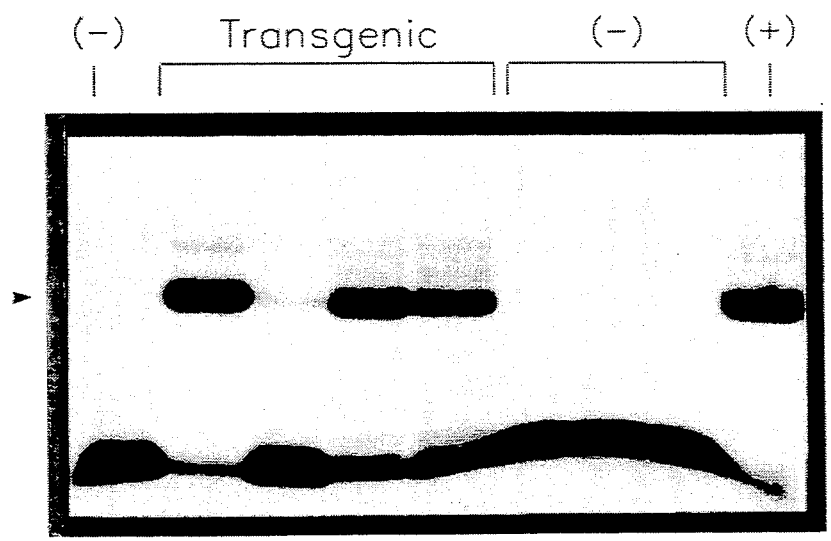
Figure 13:
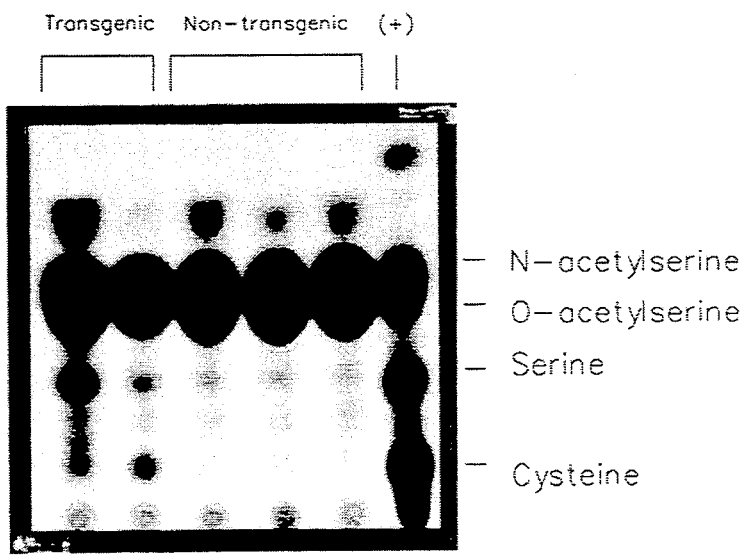

FIG. 12 illustrates the polymerase chain reaction used to detect transgenic animals FIG. 13 illustrates the sulphydrylase assay in transgenic sheep tissue.

FIG. 14 illustrates that this DNA sequence of the cysK gene had been obtained from the GenBanK nucleotide database (Accession no. M21450). The restriction sites HaeIII and HinDIII are underlined. Translation of the cysK gene begins from the AUG triplet at position 1255 and ends at 2226.

EXAMPLE 1

Materials and Methods

Plasmid and expression vector constructs

Plasmid pRSM8 was a gift of N. Kredich (Duke University Medical Centre, Durham, N.C.) containing a BamHI/HindIII insert, 2.3 kb long. Plasmids pE, pKB and pKH were derived from pRSM8 by deletion of a 0.9 kb EcoRl, a 1.2 KpnI/BamHI and 1.2 kb KpnI/HindIII fragment respectively, followed by blunt-end ligation.

The 1.5 kb EcoRl/BamHI insert fragment from pRSM8 was subjected to a partial DdeI digest and a 0.98 kb DdeI/EcoRi fragment spanning the region from nucleotide 518 to 1497 of the cysE gene sequence (see FIG. 2) was isolated. pGEM-cysE was generated by introducing this DdeI/EcoRl fragment by blunt-end ligation into the SmaI site of pGEM-2 (Promega).

Figure 3:
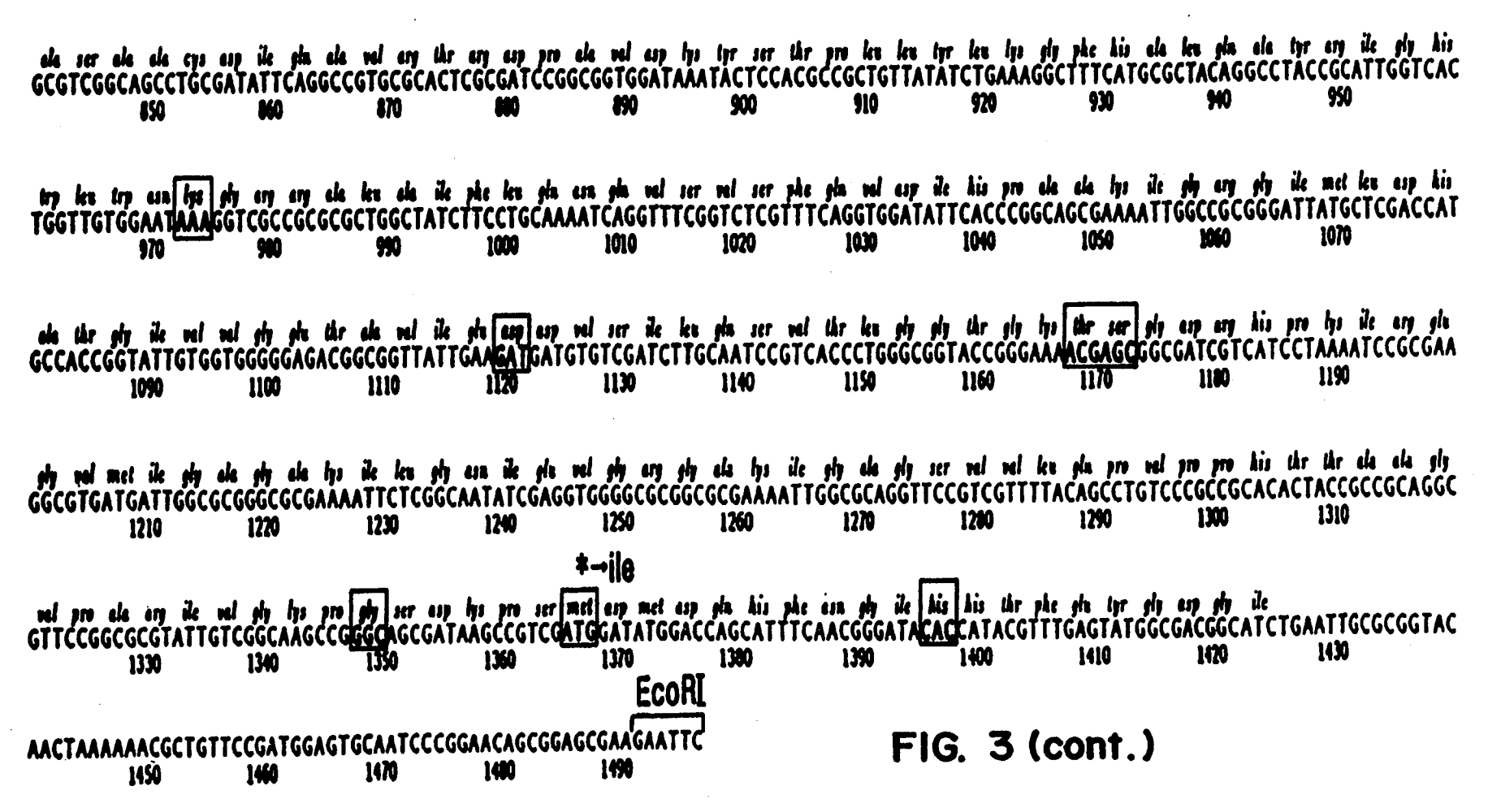

Similarly, the DdeI/EcoRIO fragment described above was used to construct two expression plasmids (see FIG. 3 for testing in cell culture. pJL-E was an SV40-based vector derived from pJL4 and contained the cysE gene sequence inserted at the SalI site of the polylinker downstream to the SV40 late promoter. A 133 bp HpaI/BamHI isolated from pSV2CAT encompassing the polyadenylation signal sequences for SV40 early transcripts was inserted into the SmaI site of the polylinker in pJL4 to provide necessary 3' end processing. pGER001 contained the cysE gene flanked upstream by the 0.85 kb RSVLTR promoter sequence and downstream by a 0.6 kb sequence from the 3' flanking region of the human growth hormone gene. This construct was derived from pRSVN.03 (a gift of A. Robins) by blunt-end cloning into the BamHI site and it also contained the neomycin-resistance gene enabling selection of stably-transfected cell lines with G418.

Cell Culture and DNA transfection

All cell lines were grown in monolayer cultures in a humidified incubator at 37° C. in the following media supplemented with 10% (v/v) foetal calf serum: Hela and SV-40-transformed sheep ruminal epithelial (RE) cells were grown in Dulbecco's modified Eagle's medium (DMEM-Gibco) and Chinese hamster ovary (CHO) cells in Ham's F12 medium (Gibco).

The expression vector constructs were transfected (0.5–2 ug of DNA) into RE and Hela ($4 \times 10^6$) cells using DEAE-Dextran at a concentration of 500 ug/ml.

Complementation testing and size estimation of the cysE gene product

Figure 1:
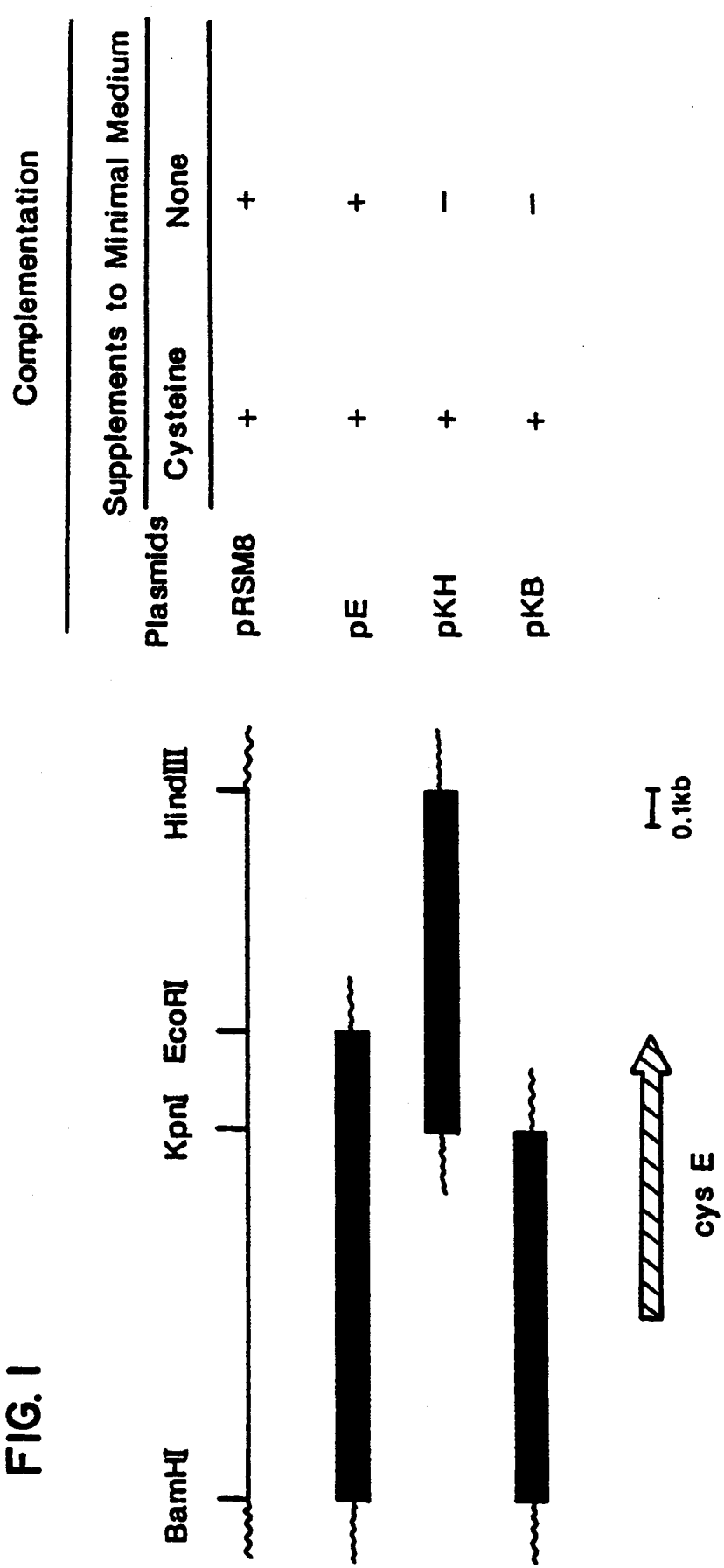
FIG. 1 is a restriction map of the cysE gene of *Salmonella typhimurium*

The cysE locus of *Salmonella typhimurium* containing the structural gene for serine acetyltransferase (SAT) had been cloned previously (Monroe and Kredich, 1988). The plasmid pRSM8 containing a 2.3 kB BamHI/HindIII insert and the derived deletion plasmids (as shown in FIG. 1) were transformed in to JM70, an *E. coli* strain carrying a cysE mutation which cannot grow in media unless cysteine has been added. Experiments have established that the cysE functional gene was centrally located within the 2.3 kb BamHI/HindIII insert, but more precisely, it was wholly contained within the 1.5 kb BamHI/EcoRI fragment and spanned the KpnI restriction site.

Sequence analysis of the cysE gene from *Salmonella typhimurium*

Figure 2A:
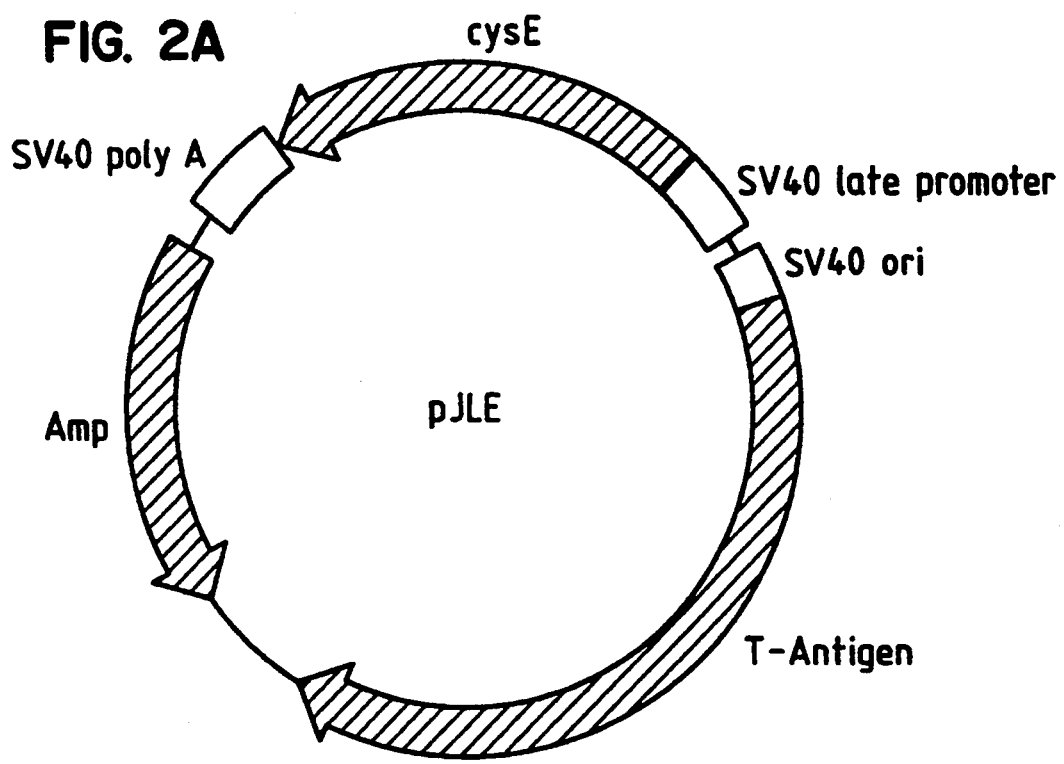
FIGS. 2A and 2B illustrates the restriction maps for plasmids pJLE and pGER001.
Figure 2B:
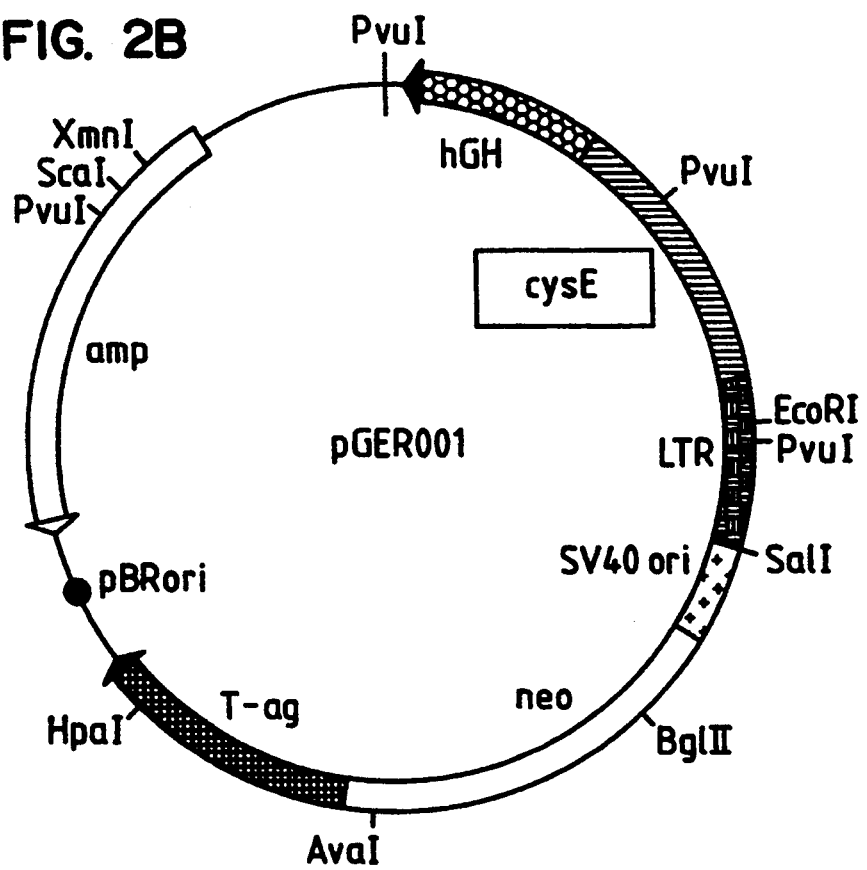

The complete nucleotide sequence of the BamHI/HindIII insert of pRSM8 was determined and the DNA sequence within the relevant 1.5 kb BamHi/EcoRI fragment is shown in FIG. 2. The coding region of the cysE gene within the pRSM8 insert (as shown in FIG. 1) was located by direct comparison with the recently published *E. coli* cysE gene (Denk and Bock, 1987). The coding regions from both strains are identical in length with an open reading frame of 819 bp encoding a protein of 273 amino acids. Homology within the protein-coding regions is 84% with most of the differences resulting in silent-site mutations. Out of 273 amino acids, only 10 changes (randomly distributed) were observed (see FIG. 2) between the two bacterial strains.

To determine the 5' end of the *S. typhimurium* cysE transcript, a primer-extension experiment was carried out using a 24-base synthetic oligomer complementary to a region surrounding the ATG initiation codon (see FIG. 2). Primer extension on wild type *S. typhimurium* total RNA (data not shown) indicated extension products which coincided in length with the 5' end of the *E. coli* cysE transcription start site which has been mapped at a position 118 bases upstream to the AUG codon (Denk and Bock, 1987).

Expression of SAT activity in mammalian cells

Two different expression plasmids pJLE and pGER001 (see FIG. 3) were used to transfect Hela, CHO and sheep RE (ruminal epithelial) cells to examine transient expression of the cysE gene in these different cell types. Cell extracts from each transfected cell line showed SAT activity with both cysE constructs (FIG. 4). In all three cases, the level of cysE expression was greatest when the bacterial gene was fused to the LTR promoter (pGER001 construct) of Rous Sarcoma virus (RSV) rather than the SV40 late promoter (pJL-E construct). Plasmid pJL-E synthesizes the cysE product and is an SV40-based vector producting T-antigen which stimulates replication in DNA molecules containing SV40 origin of replication. However, even though the pJL-E vector can replicate to thousands of copies per cell, it produces cysE at a level lower than that from pRSVN.03-E indicating that the RSVLTR sequence is a strong promoter of cysE expression in cells even though the vector molecule does not replicate. In fact, the lack of vector replication in pRSVN.03-E transfected CHO cells does not diminish cysE expression levels to lower than that seen for pRSVN.03-E transfected RE cells (see FIG. 4), in which the vector is capable of replication (due to the presence of an SV40 ori sequence used to promote the neomycin-resistance gene) in this SV40-transformed sheep cell line. Further to these results, stable transformation of CHO cells with pRSVN.03-E produces cell extracts which give almost complete conversion of input $^{14}$C-serine to $^{14}$C-OAS in the SAT assay (data not shown).

EXAMPLE 2

Materials and Methods (a) Chemicals and enzymes

Radiochemicals, Escherichia coli DNA polymerase I (Klenow fragment), SP6 RNA polymerase, T4 DNA ligase and the universal sequencing primer which were purchases from Biotechnology Research Enterprises of S.A. Pty. Limited (BRESA). The oligonucleotides were custom synthesized by BRESA.

(b) Media

Cultures were routinely grown in Luria Broth (Ref.) or in 2xYT Medium (10 g yeast extract, 16 g tryptone and 5 g sodium chloride, per liter).

(c) Bacterial strains and genomic library

The *E. coli* strain NK3 (Hulanicka et. al., 1986) was a gift from N. Kredich, and it carried the cysK cysM mutations. The *S. typhimurium* strain 9002(Ref.) was used for preparing the bacterial cell extract used in sulphydrylase assays. The 1059, library of *S. typhimurium* LT2 genomic DNA, obtained as a gift from R. Maurer through P. Reeves, has been described (Maurer et. al., 1984).

(a) Isolation of the gene

A 1059 library of the *S. typhimurium* LT2 genomic DNA formed the source of cysM gene. Phage clones were isolated by lytic complementation of the cysK cysM strain NK3, digested the DNA with SalI and shotgun cloned into pBR322. A plasmid, pCS901, capable of complementing the defect in NK3 was selected (FIG. 5) for further studies. Since cysK and cysM, together or singly, would confer Cys+ character to NK3 it was difficult to say which of these genes was cloned in pCS901. However, further observations suggested that it carried cysM but not clear cysM but not cysK.

(b) Nucleotide Sequence of DNA containing the cysM gene

The entire DNA sequence of the 4.7 kb insert in pCS901 was determined in order to locate the coding region of cysM as well as to facilitate in the modifications planned for the 5' and 3' ends of the gene for expression in eukaryotic systems. FIG. 6 gives the sequence of a SacII-PvuII fragment which, on cloning in the two alternative orientations in pBR322, produced functional OASS-B and complemented NK3. The sequence displayed a single open reading frame (ORF) of 40000 MW starting from the AUG at 241. Computer search for prokaryotic promoter did not identify any potential promoter but a hairpin loop structure ( G=11.31 KCal/mol) with a string of 6 T's was found between sequence positions 369 and 404 (FIG. 4). Immediately following this potential rho- independent transcription terminator, and separated from each other by 15 bases, were sequences having good homology to the consensus sequences for the −35 and −10 regions of prokaryotic promoter (FIG. 7).

(c.1) Construction of the plasmid pCS920

In the DNA between the SacII and PvuII there were two AUG codons, at sequence positions 228 and 241, preceding the predicted start of cysM (FIG. 6). For testing in eukaryotic system these codons must be deleted if translations were to initiate from the chosen AUG at position 565. The first AUG, at 228, was changed to an AUC by oligonucleotide directed mutagenesis at the same time creating a SmaI site at 230. The DNA for effecting this mutations was originally cloned in M13tg131 (Amersham) and, after sequence verifying the change, was cloned back into pBR322 to generate pCS916 (FIG. 5). This plasmid was capable of complementing the Cys− strain NK3, indicating that the cysM gene was intact. Now, a deletion from the newly created SmaI to the HaeII site at 386 (one of many on pCS916) was effected by partial digestion with HaeII and religating the end to the SmaI end. The resulting plasmid, pCS919, was restriction digested to verify the loss of DNA between these two sites. As this plasmid also was expressing cysM (FIG. 8) it indicated that the translation of the gene was downstream to the HaeII site at 386. Two DNA fragments, BssHII (Sequence position 24 in FIG. 6) to BamHi, and ClaI (sequence position 561) to BamHi, taken from pCS919, were cloned into the SmaI site of the SP6/T7 promoter vector pGEM2 (Promega Corporation) to generate pCS920 and PCS921, respectively.

(c.2) In vitro Eukaryotic translation of cysM

T7 transcripts made from EcoRI cut DNAs of these plasmids were translated with RRL and found that PCS920 produced at 29 kDal protein indentical in size to the cysM gene product where pCS921 produced a slightly shorter polypeptide (FIG. 8). This indicated that the start site of translation of cysM was located to the left of the ClaI site at 561. No AUG codon is present in this region but it was established that the inframe GUG codon, at 541, was the initiation codon for the gene.

(d) Expression of cysM in mammalian cell line

Although the plasmids carrying the cysM gene complemented the strain NK3 it could still be argued that this gene was a positive regulator of the sulphydrylase B rather than its structural gene. It was therefore decided to test the expression in cultured mammalian cells. The gene/promoter construct (pGER002) for this testing, shown in FIG. 5 carries the Rous Sarcoma Virus LTR (RSVLTR) at the 5' side and the transcription termination and polyadenylation signals from human growth hormone (hGH) at the 3' side of the cysM gene. Normal transcription and translation of the gene was therefore expected in stably transfected Chinese Hamster Ovary (CHO) cells. The plasmid was linearized with SalI, transfected by electroproporation and five G418 resistant colonies of cells, which contain integrated copies of the plasmid, were selected and used for preparing crude cell extract. The cell extract was then tested in vivo for sulphydrylase activity and found that all five isolates were producing active enzyme (FIG. 9) presence of sylphydrylase activity in these cells provided that the gene was actively transcribed and translated and also proved that cysM was the structural gene for sulphydrylase B.

Expression of cysM in transgenic mice

Figure 9B:
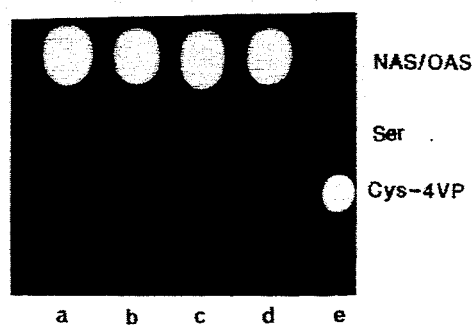

Testing the gene in transgenic mice would expose any potential deleterious effect caused by the constitutive expression of sulphydrylase in animal tissue and demonstrate the usefulness or otherwise of the gene in fugure sheep transgenesis. For this purpose the gene, together with the RSVLTR promoter and the hGH sequences, was excised from pGER002 and the DNA used for microinjection into mouse embryous. Tail sections from progeny mice were homogenized and the crude extract assayed for sulphydrylase activity (FIG. 9). Presence of the enzyme activity in some of these extracts indicated that these mice were transgenic and expressing the gene. Transgenes were also confirmed by DNA:DNA hybridizations using cysM specific probe (FIG. 6). A 2.9 kb band hybridizing to the probe points out that there are multiple copies of tandemly integrated DNA, and represents the fragment between the EcoRI siges which occurs once in the RSVLTR promoter.

EXAMPLE 3

Construction of Plasmid pGER003

A 3.3 kb SalI/ScaI fragment may be excised from pGER002 and inserted into the ScaI site of pGER001 by blunt-end ligation. Recombinants were selected on media containing ampicillin such that only those clones containing a tandem arrangement of the CysE and CysM genes (i.e. recombinants in which the β-lactamase or amp$^r$ gene was restored) were viable. The product was designated plasmid pGER003 (FIG. 10).

EXAMPLE 4

The plasmid pGER004 carries the two cysteine biosynthesis genes, cysE and cysM, under the transcriptional control of the RSVLTR promoter. Plasmid pGER004 is illustrated in FIG. 11. Its preparation is as follows:

a. The cysE gene containing DNA, isolated as a 1.5 kb BamHI/ExoRI fragment from the plasmid pRSM8 (N. Kredich, personal communication), was partially digested with DdeI and a 0.98 kb DdeI/EcoRI fragment which contained the entire coding region of cysE was isolated and blunt ligated into the BamHI site, which resides in between the RSVLTR promoter and the 3' untranslated region from the human growth hormone (hGH), in the plasmid pRSVΔAH. The orientation of the insert which would permit the correct initiation and termination of transcription of cysE was selected.

b. The cysM gene was excised from the Salmonella typhimurium DNA as a SacII/PvuII fragment and cloned into the EcoRV site of M13tg131 (Amersham). A 153 bp fragment containing the SV40 (early) polyadenylation site, was cloned downstream to the EcoRV site in the appropriate orientation. Oligonucleotide directed mutagenesis was performed on the ssDNA from this M13 clone to create a SmaI and a HaeII site, a 158 bp section of DNA was deleted to remove the two upstream AUG codons present on the DNA. The GUG initiation codon of the cysM gene was mutated, using oligonucleotide directed mutagenesis, to AUG, and while doing this an NcoI site was created. The sequence surrounding the AUG codon now read as, ACCATGG, which is the "perfect" consensus sequence for eukaryotic translation initiation. The DNA was excised, as an HindII/ExoRI fragment and cloned into the plasmid pGEM2 to test the efficiency of in vitro transcription and translation. Fragment isolated from this pGEM2 clone was ligated into the BamHI site of pRSVΔAH. The orientation which would permit the correct initiation and termination of transcription of cysM was selected.

c. The cysM gene, together with the LTR and hGH sequences, was excised from the plasmid in (b) as a ScaI/SalI fragment, blunt ligated into the SalI site of the plasmid in (a) and the orientation determined. This plasmid was tested for cysteine synthase activity in tissue culture cells after stable transfection of CHO cells.

A still further improvement may be achieved by replacing the cysM gene with a related gene, cysK, to produce a further plasmid construct pGER005.

EXAMPLE 5

Isolation of cysK and Construction of pGER005

The bacterial gene, cysK may be substituted for cysM, since its protein product (O-acetylserine sulphydrylase) has a higher affinity for the substrate, O-acetylserine, as compared to the cysM gene product. In the tissues of the transgenic animals this higher affinity may be an advantage if the substrate concentration is low.

The following is a detailed plan for the isolation and construction of cysK for expression in eukaryotic cells.

We have received the DNA sequence and a plasmid clone of the cysK gene as an unqualified gift from N. Kredich. Examination of the sequence revealed that a HaeIII site occurred 4 bases to the left of the AUG initiation codon of the gene. Two other HaeIII sites occur in the coding region and a third at about 50 bases after the termination codon. Partial digestion with HaeIII, to isolate the intact coding region of the gene, and blunt ligation into the SalI site of M13mp18 was undertaken. This cloning generates a sequence very similar to the consensus sequence for eukaryotic translation (the "Kozak sequence") near the initiation codon. After verifying, by sequencing, that the correct fragment has been cloned the sequence was excised and blunt ligated into the BamHI site of pRSVΔH. After demonstrating the enzyme activity for this construct a ScaI/SalI fragment from this plasmid was blunt ligated into the SalI site of the plasmid in (a) Example 4 above to generate pGER005 which is similar to pGER004 except that it has cysK in place of cysM. Tissue culture expression and sheep transgenesis with the new construct may be compared to pGER004 to assess the increase in efficiency.

EXAMPLE 6

Production of Transgenic Sheep

Microinjections of a fragment from pGER004 carrying the cysM and cysK genes began in 1989 and by Oct. 30, 1989, thirty-five lambs have been analysed and seven have been found to carry the intergrated genes. This is the highest-yield of transgenic sheep reported worldwide. The polymerase chain reaction PCR was used to detect the transgenic lambs and one of the results is shown in FIG. 12.

Experiments of a limited kind have been carried out to detect whether the pathway is operating in the sheep. Samples of tail tissue have been extracted and incubated with $^{14}C$-serine and sulphide as substrates. FIG. 13 suggests that cysteine was synthesized. More extensive evaluation is planned for 1990 such as:

a. biopsies of liver, gut (including rumen) and muscle and assaying for cysteine biosynthesis enzymes;

b. injection of $^{35}S$-sulphide into the transgenic lambs and assaying for $^{35}S$-cysteine.

I claim:

1. A plasmid including as operably joined components:
   (a) a eukaryotic plasmid cloning vector;
   (b) a first sequence of DNA encoding the enzyme serine acetyltransferase (SAT) or a functionally active part thereof;
   (c) a second sequence of DNA encoding the enzyme O-acetylserine sulphydrylase (OASS) or a functionally active part thereof;
   (d) a third sequence of DNA encoding a eukaryotic promoter region; and
   (e) a fourth sequence of DNA derived from human growth hormone (hGH) encoding the transcription, termination and polyadenylation signals thereof.

2. A plasmid including as operably joined components:
   (a) a eukaryotic plasmid cloning vector;
   (b) a first sequence of DNA encoding the enzyme serine acetyltransferase (SAT) or a functionally active part thereof;
   (c) a second sequence of DNA encoding the enzyme O-acetylserine sulphydrylase (OASS) or a functionally active part thereof;
   (d) a third sequence of DNA encoding a eukaryotic promoter which directs gene expression in the ruminal mucosa cells; and,
   (e) a fourth sequence of DNA derived from human growth hormone (hGH) encoding the transcription, termination and polyadenylation signals thereof.

3. A plasmid according to claim 2 wherein the first sequence of DNA includes the cysE gene from *Salmonella typhimurium* or a fragment thereof encoding a functionally active product; and, the second sequence of DNA includes the cysM or cysK gene from *Salmonella typhimurium* or a fragment thereof encoding a functionally active product.

4. A plasmid according to claim 2 wherein the third DNA sequence of DNA is selected from the group consisting of the long terminal repeat (LTR) promoter of *Rous sarcoma* virus and the SV40 late promoter.

5. A plasmid according to claim 2 wherein the first sequence of DNA includes a 0.98 kb DdeI/EcoRI DNA fragment encoding the cysE gene as described in FIG. 3 or part thereof encoding a functionally active product.

6. A plasmid according to claim 2 wherein the second sequence of DNA includes a SacII/PvuII DNA fragment encoding the cysM gene as described in FIG. 6, or part thereof encoding a functionally active product.

7. A plasmid according to claim 2 wherein the second sequence of DNA includes HaeIII/HaeIII DNA fragment encoding the cysK gene as described in FIG. 14, or part thereof encoding a functionally active product.

* * * * *

UNITED STATES PATENT AND TRADEMARK OFFICE
CERTIFICATE OF CORRECTION

PATENT NO. : 5,360,742  
DATED : November 1, 1994  
INVENTOR(S) : George E. Rogers It is certified that error appears in the above-indentified patent and that said Letters Patent is hereby corrected as shown below:

Column 1, line 55, after the word "including", insert --:--.
Column 1, lines 67 and 68, delete "endogeneous" and insert therefor --endogenous--.
Column 2, line 40, after the word "including", insert --:--.
Column 2, line 61, delete "EcoR1" and insert therefor --EcoRI--.
Column 2, line 63, delete "EcoR1" and insert therefor --EcoRI--.
Column 3, line 40, delete "Further more" and insert therefor --Furthermore--.
Column 3, line 43, delete "cysterine" and insert therefor --cysteine--.
Column 3, line 56, delete "cysterine" and insert therefor --cysteine--.
Column 4, line 1, after the word "including", insert --:--.
Column 4, lines 43 and 44, delete "endogeneous" and insert therefor --endogenous--.
Column 4, line 49, delete "fertilised" and insert therefor --fertilized--.
Column 5, line 61, delete "OASSB" and insert therefor --OASS-B--.
Column 6, line 55, delete "EcoR1" and insert therefor --EcoRI--.
Column 6, line 57, delete "EcoRi" and insert therefor --EcoRI--.
Column 6, line 60, delete "EcoR1" and insert therefor --EcoRI--.
Column 6, line 62, delete "EcoRIO" and insert therefor --EcoRI--.
Column 7, line 14, delete "ahumidified" and insert therfor -- a humidified--.
Column 7, line 24, after the word "product", insert --.--.

UNITED STATES PATENT AND TRADEMARK OFFICE
CERTIFICATE OF CORRECTION

PATENT NO. : 5,360,742
DATED : November 1, 1994
INVENTOR(S) : George E. Rogers

It is certified that error appears in the above-indentified patent and that said Letters Patent is hereby corrected as shown below:

Column 7, line 28, delete "kB" and insert therefor --kb--.
Column 7, line 36, delete "EcoR1" and insert therfor --EcoRI--.
Column 7, line 42, delete "BamHi/EcoRI" and insert therfor --BamHI/EcoRI--.
Column 8, line 8, delete "producting" and insert therefor --producing--.
Column 9, line 27, delete "this" and insert therefor --these--.
Column 9, line 41, delete "BamHi" and insert therefor --BamHI--.
Column 9, line 42, delete "BamHi" and insert therefor --BamHI--.
Column 9, line 45, delete "PCS921" and insert therefor --pCS921--.
Column 9, line 49, delete PCS920" and insert therefor --pCS920--.
Column 10, line 52, delete "ExoRI" and insert therefor --EcoRI--.
Column 10, line 60, delete "pRSVΔAH" and insert therefor --pRSV H--.
Column 11, line 17, delete "pRSVΔAH" ' and insert therefor --pRSV H--.

Signed and Sealed this

Twenty-sixth Day of September, 1995

Attest:

BRUCE LEHMAN

*Attesting Officer*     *Commissioner of Patents and Trademarks*